(12) United States Patent
Richelsoph (10) Patent No.: US 8,529,602 B2
(45) Date of Patent: Sep. 10, 2013

(54) SELF-CONTOURING SPINAL ROD

(75) Inventor: Marc Evan Richelsoph, Memphis, TN (US)

(73) Assignee: Aesculap AG & Co. KG, Tuttlingen (DE)

( * ) Notice: Subject to any disclaimer, the term of this patent is extended or adjusted under 35 U.S.C. 154(b) by 1215 days.

(21) Appl. No.: 11/881,293

(22) Filed: Jul. 26, 2007

(65) Prior Publication Data

US 2008/0091214 A1  Apr. 17, 2008

Related U.S. Application Data

(63) Continuation of application No. PCT/EP2006/000673, filed on Jan. 26, 2006.

(60) Provisional application No. 60/647,151, filed on Jan. 26, 2005.

(51) Int. Cl.
*A61B 17/70* (2006.01)

(52) U.S. Cl.
USPC .......................................... 606/254; 606/259

(58) Field of Classification Search
USPC .......................................... 606/246, 250–279
See application file for complete search history.

(56) References Cited

U.S. PATENT DOCUMENTS

| | | | | |
|---|---|---|---|---|
| 4,047,523 A | * | 9/1977 | Hall | 606/276 |
| 4,422,478 A | * | 12/1983 | Pentney et al. | 138/168 |
| 4,526,666 A | * | 7/1985 | Bianchi et al. | 29/854 |
| 4,570,618 A | * | 2/1986 | Wu | 606/263 |
| 4,697,582 A | * | 10/1987 | William | 606/254 |
| 4,815,453 A | * | 3/1989 | Cotrel | 606/261 |
| 5,047,025 A | * | 9/1991 | Taylor et al. | 606/31 |
| 5,300,075 A | | 4/1994 | Gordon et al. | |
| 5,417,690 A | * | 5/1995 | Sennett et al. | 606/74 |
| 5,460,883 A | * | 10/1995 | Barber et al. | 428/370 |
| 5,636,551 A | * | 6/1997 | Davidson et al. | 74/502.5 |
| 5,704,936 A | * | 1/1998 | Mazel | 606/254 |
| 5,997,542 A | * | 12/1999 | Burke | 606/74 |
| 6,162,237 A | * | 12/2000 | Chan | 606/198 |
| 6,290,700 B1 | * | 9/2001 | Schmotzer | 606/263 |
| 7,604,653 B2 | * | 10/2009 | Kitchen | 606/257 |
| 2003/0148247 A1 | * | 8/2003 | Sicurelli et al. | 433/220 |
| 2004/0049190 A1 | * | 3/2004 | Biedermann et al. | 606/61 |

(Continued)

FOREIGN PATENT DOCUMENTS

FR   2 702 363       9/1994
FR   2715825   *   8/1995

(Continued)

OTHER PUBLICATIONS

PCT International Search Report of PCT/EP2006/000673; Completed Apr. 26, 2006; Mailed May 8, 2006.

*Primary Examiner* — Jerry Cumberledge
(74) *Attorney, Agent, or Firm* — RatnerPrestia (57) ABSTRACT

A self-contouring spinal rod assembly. The assembly has a proximal end, a distal end, and a length extending between the proximal end and the distal end. A plurality of rod elements extend along the length, such that each of the plurality of rod elements is in contact with an adjacent rod element. The plurality of rod elements are fixed against movement relative to each other at the distal end. The plurality of rod elements are movable relative to each other along a length proximal the distal end. A method of assembling the spinal rod assembly is also provided.

38 Claims, 6 Drawing Sheets

(56) References Cited

U.S. PATENT DOCUMENTS

| | | | |
|---|---|---|---|
| 2004/0143264 A1* | 7/2004 | McAfee | 606/61 |
| 2004/0215191 A1* | 10/2004 | Kitchen | 606/61 |
| 2004/0236328 A1* | 11/2004 | Paul et al. | 606/61 |
| 2004/0267260 A1* | 12/2004 | Mack et al. | 606/61 |
| 2005/0065516 A1* | 3/2005 | Jahng | 606/61 |
| 2005/0096652 A1* | 5/2005 | Burton | 606/61 |
| 2005/0261686 A1* | 11/2005 | Paul | 606/61 |
| 2006/0069390 A1* | 3/2006 | Frigg et al. | 606/61 |
| 2006/0282073 A1* | 12/2006 | Simanovsky | 606/61 |
| 2007/0129729 A1* | 6/2007 | Petit et al. | 606/61 |

FOREIGN PATENT DOCUMENTS

| | | |
|---|---|---|
| FR | 2715825 A1 * | 8/1995 |
| FR | 2 745 706 | 9/1997 |
| FR | 2 806 615 | 9/2001 |
| WO | WO 9944527 A1 * | 9/1999 |
| WO | WO 02/085217 | 10/2002 |
| WO | WO 2004/096066 | 11/2004 |
| WO | WO 2005092222 A1 * | 10/2005 |

* cited by examiner

SELF-CONTOURING SPINAL ROD

This Continuation Application claims priority to International Application PCT/EP2006/000673 filed Jan. 26, 2006 pursuant to 35 U.S.C. §365(c), which claims priority to U.S. Provisional Application 60/647,151 filed Jan. 26, 2005, the contents of both being incorporated by reference herein.

FIELD OF THE INVENTION

The present invention relates generally to a spinal rod, and more specifically, the invention relates to a self-contouring spinal rod that reduces or eliminates rod contouring during insertion while providing sufficiently rigid support of a spinal implant system.

BACKGROUND OF THE INVENTION

It can be appreciated that spinal rods have been in use for years. Typically, spinal rods are comprised of rods constructed from titanium and stainless steels. However, one problem with a conventional spinal rod is that the rigidity of the rod makes contouring the rod difficult and time consuming to insert into the spine. Another problem with conventional spinal rods is the inability to perform multiple level fusions through a minimally invasive approach. Still another problem with conventional spinal rods is that the required contouring of the rod to meet patient anatomy often creates a non-uniform bend or bends (i.e. kinks) that decrease the strength of the rod.

In spinal fixation, screw or hook components are attached to the spine and connected to a rigid rod. This allows the alignment of the spine to be adjusted and/or held in a specific manner to allow fusion to occur. However, the natural anatomy of the spine does not allow hooks and screws to be connected in a straight line. The lordotic curve requires that a rod be contoured to match this lordosis, particularly on multiple level fusions. In addition, the pedicies vary in location and angle such that screws placed in the pedicles do not always line up in multiple level fusions. Therefore, for proper connection of all spinal components while maintaining the natural curvature of the spine, the rod must be contoured in multiple planes. In addition, this becomes much more difficult for minimally invasive surgical techniques, where the rod is inserted into the spinal components through a minimal incision. The rod has to be very carefully contoured, and the number of levels or vertebrae fused must be kept to a minimum. Although systems exist to help template and guide the rod into screw bodies, these procedures are limited and are often difficult and time consuming. Although these devices may be suitable for the particular purpose to which they address, they are not as suitable to provide a device that reduces or eliminates rod contouring during insertion while providing sufficiently rigid support of a spinal implant system.

SUMMARY OF THE INVENTION

The present invention includes an assembly of a plurality of rod elements forming a spinal rod assembly having proximal end, a distal end, and a length extending between the proximal end and the distal end. A plurality of rod elements extend along the length, such that each of the plurality of rod elements is in contact with an adjacent rod element. The plurality of rod elements are fixed against movement relative to each other at the distal end. The plurality of rod elements are movable relative to each other along a length proximal of the distal end.

Also, the present invention provides a self-contouring spinal rod assembly comprising a rod bundle having a distal end, a proximal end, and a length extending between the distal end and the proximal end. A tip is fixedly connected to the distal end. A sheath is wrapped around the rod bundle, proximal of the distal end.

Additionally, the present invention provides a method of assembling a spinal rod assembly. The method comprises the steps of providing a plurality of rod elements, bundling the plurality of rod elements in a bundle, fixedly connecting distal ends of the plurality of rod elements together, and disposing a covering over the plurality of rod elements, proximal the distal ends.

BRIEF DESCRIPTION OF THE DRAWINGS

The foregoing summary, as well as the following detailed description of preferred embodiments of the invention, will be better understood when read in conjunction with the appended drawings, which are incorporated herein and constitute part of this specification. For the purposes of illustrating the invention, there are shown in the drawings embodiments that are presently preferred. It should be understood, however, that the invention is not limited to the precise arrangements and instrumentalities shown. In the drawings, the same reference numerals are employed for designating the same elements throughout the several figures. In the drawings.

DETAILED DESCRIPTION OF THE INVENTION

Certain terminology is used herein for convenience only and is not to be taken as a limitation on the present invention. The terminology includes the words specifically mentioned, derivatives thereof and words of similar import. As used herein, the term "distal" is defined to mean a direction closer to a tip of a rod assembly as described herein and "proximal" is defined to mean a direction farther from the tip of the rod assembly as described herein. Further, the term "rod element" may mean wires, shafts, and bars, or any other elongated device, in addition to rods. The following describes preferred embodiments of the invention. However, it should be understood based on this disclosure, that the invention is not limited by the preferred embodiments of the invention.

Referring to the Figures generally, a self-contouring spinal rod assembly is shown. The rod assembly is used in a spinal implant to support the spinal implant. The rod assembly is inserted into a screw, a hook, or other spinal components during spinal surgery. The rod assembly provides flexibility during insertion, however, once the rod assembly is inserted into the spinal implant bodies, the flexibility of the individual rod elements making up the rod assembly is no longer an advantage. Maintaining alignment of the vertebral bodies to allow fusion becomes the key factor. The more rigid rod assembly according to the present invention is formed by compressing individual rod elements against each other, thereby minimizing or preventing the rod elements from moving independently. This allows the curvature generated during insertion of the rod assembly into the spinal implant bodies to become fixed and rigid. The spinal loads are then distributed over the entire rod assembly 100.

Figure 1:
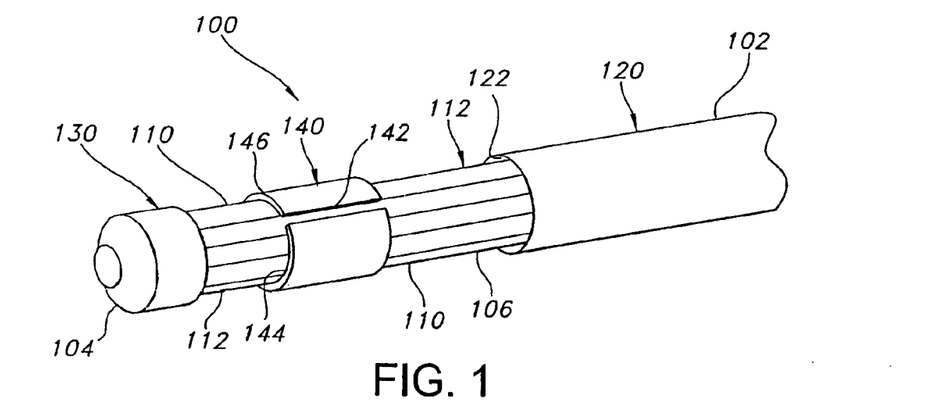
FIG. 1 is a perspective view of a spinal rod assembly according to a first embodiment of the present invention.
Figure 2:
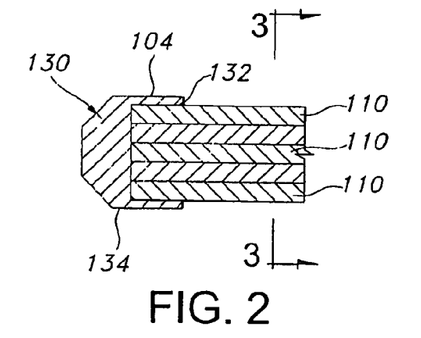
FIG. 2 is a side view, in section, of a distal tip of the spinal rod assembly of FIG. 1.

Referring now to FIGS. 1 and 2, a first embodiment of a spinal rod assembly 100 according to the present invention is shown. The spinal rod assembly 100 includes a proximal end 102, a distal end 104, and a length 106 extending between the proximal end 102 and the distal end 104.

The rod assembly 100 comprises at least two or more small diameter rods elements 110, forming a bundle; a covering, such as an external flexible sheath 120, that is slid over the rod elements 110 either temporarily during insertion and removed after insertion or permanently fixed to the assembly 100; and a tip 130 located at the distal end 104 that holds the individual rod elements 100 together and provide a means to guide the rod elements 110 into screw or hook bodies or attached to the tip 130 to provide the appearance of a single component (with the individual rod elements 110 not visible). An external collar 140 may also act as a covering and may be used to provide additional support to the rod elements 110 by reinforcing and squeezing the rod elements 110 together.

The tip 130 provides a means of connecting the rod elements 110 at one location. In addition, the tip 130 provides a means to connect the sheath 120 when the sheath 120 is a permanent part of the rod assembly 100. A chamfer or radius on the external surface of the tip 130 allows easier insertion into spinal implant components. Although tip 130 is preferred, it is possible to avoid the use of the tip 130 and bond the rod elements 110 together along with the sheath 120, by various manufacturing techniques.

Compression of the individual rod elements 110 against each other may be performed in numerous ways. Screw and hook bodies having the ability to compress the rod elements 110 may be used without any additional components. Split collars 140, or collapsible collars may be used to provide a uniform load to the rod elements 110 inside a screw or hook body that would normally not exert a sufficiently uniform load. Therefore, the collar 140 acts as an adapter to systems that use a set screw, nut, or other locking means that does not function sufficiently for locking the rod elements 110. The collar 140 is also designed to lock the individual rod elements 110 where there are no implants or where there are large distances between implants.

As seen in FIG. 1, a plurality of rod elements 110 extend along the length 106. The rod elements 110 are bundled together such that adjacent rods elements 110 are in physical contact with each other. By using a smaller rod diameter, flexibility of the rod increases, but the load carrying capacity decreases along with the fatigue life and the ability to keep the alignment of the spinal implants during fusion. Therefore, to form a more flexible rod assembly 100 that can elastically bend and adjust to the spinal anatomy, a rod assembly 100 is provided that comprises multiple smaller diameter rod elements 110 that carry the load. Using a multiple rod element assembly requires a balance of flexibility verses load carrying ability. These series of rod elements 110 form a flexible core. By allowing the individual rod elements 110 to move independently, the core remains extremely flexible. Of course, the flexibility of the core is dependent on the diameter of the rod elements 110 and material used in the rod elements 110. By using a stronger material to form the rod elements 110, the amount of load or stress that the rod assembly 100 can carry increases according to the increase in tensile and yield strengths.

Figure 3:
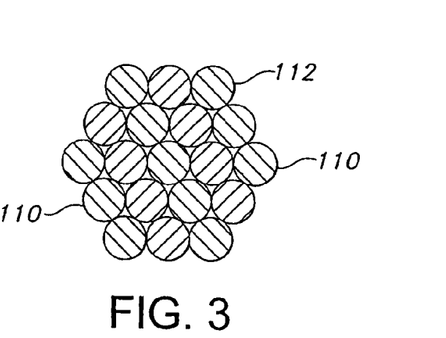
FIG. 3 is a sectional view of the spinal rod assembly taken along lines 3-3 of FIG. 2.

The rod elements 110 may have a generally circular cross section, as seen in FIG. 3. The rod elements 110 may be constructed from a biocompatible metal, such as titanium, $Ti_6Al_4$, stainless steel, Nitinol, or other suitable material. One advantageous rod construction is to manufacture the rod elements 110 using a material having spring-like tendencies, so the rod elements 110 can self contour elastically.

Referring back to FIGS. 1 and 2, the rod elements 110 are fixed against movement relative to each other at the distal end 104. The rod elements 110 may be fixed to one another by welding, such as by laser beam welding. Proximal of the distal end 104, however, the rod elements 110 are free to slide and move relative to each other. Optionally, a lubricious coating 112, such as a polymer, TiN, diamond-like is coating, or other suitable, biocompatible material, may be applied to the exterior of each rod element 110 to reduce metal-to-metal contact between adjacent rod elements 110 and to facilitate slippage between adjacent rod elements 110 during use.

Desirably, at least two rod elements 110, or any appropriate number, are provided according to loading and flexibility requirements. The shape of the rod assembly 100 is preferably generally round, but with multiple rod elements 110, the shape of the rod assembly 100 may be flat, triangular, square, or any other shape desired. The arrangement of the rod elements 110 may vary as well as the materials of the individual rod elements 110. it is possible to form multiple rod elements 110 from a larger single rod by splitting the single rod into multiple rod pieces. This may be done by wire EDM, laser, or other machining techniques. However, since the rods will most likely be non-uniform and potentially have sharp edges, creating stress risers, this technique is not preferred.

The sheath 120 may be wrapped around the rod elements 110, between the proximal end 102 and the distal end 104.

The sheath 120 protects the rod elements 110 and the patient's tissue during insertion of the rod assembly 100. The sheath 120 may be fixedly attached to the rod elements 110, or, alternatively, the sheath 120 may be removable from the rod elements 110, such as during or after insertion into a patient. The sheath 120 slides over the rod elements 110 to provide for easier insertion of the rod assembly 100 into a patient. The fixedly attached sheath 120 may be fixed to the rod elements 110 by welding, compression, or other suitable manufacturing techniques.

The sheath 120 may include a generally circular interior cross section, with an interior diameter surface 122 that is sufficient to contain the rod elements 110 inserted therein. The sheath 120 is preferably constructed from a flexible, biocompatible material, such as an elastomer, a metallic or woven metallic sheath, or other suitable material. Although a flexible sheath 120 is preferred, a relatively rigid sheath may be used for initial insertion. This sheath is then withdrawn to expose the flexible rod elements 110 for insertion into the spinal components.

Alternatively, although not shown, the sheath 120 may also be formed from multiple sections. This would allow the sheath 120 to remain between spinal fixation components while removing the sheath material from within the spinal fixation components.

The sheath 120 may be free to move over the length of the rod elements 110, except at the point of fixation of the sheath 120 to the rod elements 110. To lock the rod elements 110 with the attached sheath 120, the sheath 120 is compressed against the rod elements 110, forcing the rod elements 110 into compressive contact with each other.

The tip 130 is located at the distal end 104 of the assembly 100. The tip 130 includes an inner bore 132 that is sized to accept a distal end of the rod elements 110 within and an external surface 134 for sliding through hooks, screws, or other implant components. The tip 130 is fixedly secured to the rod elements 110 to form a single bundle.

The tip 130 may be constructed to be locked to the rod elements 110 together in many manners. One method of attaching the tip 130 is to provide the bore 130 smaller than the dimensions of the bundle of rod elements 110 and then heating the tip 130 and/or cooling the rod elements 110, such that thermal expansion and/or contraction allows the rod elements 110 to slide inside the tip 130, and upon returning to ambient temperature, locks the rod elements 110 within the bore 130. Another method to secure the tip 130 to the rod elements 110 is by welding, such as laser or electron beam welding. Yet another method is by mechanical compression of the tip 130 around the rod elements 110 by crimping or otherwise forcing the inner bore 132 to engage at least one or more rod elements 110 within the bundle.

The external surface 134 of the tip 130 is preferably tapered, as is seen in FIG. 2. Such a shape assists in sliding the tip 130 through or into other spinal implants. Alternatively, the tip 130 may be pointed, radiused, or chamfered instead. in addition, the tip 130 may include indentations, holes, grooves, or other features (not shown) formed on the external surface 134 to allow instrument engagement.

Because the tip 130 is a means of securing the individual rod elements 110 into a single secure bundle, it is possible to avoid the use of a separate tip component by welding or permanently attaching the individual rod elements 110 to themselves over a short length at the distal end 104. This may be performed in such a way as to provide a taper or point at the distal end 104 such that the center rod element 110 is furthest distally and the surrounding rod elements 110 are set back in a proximal direction, effectively forming a chamfer.

The collar 140 is disposed over the rod elements 110, between the sheath 120 and the tip 130. Although not shown in FIG. 1, the collar 140 may also be disposed over the sheath 120. The collar 140 provides a means of uniform compression to the rod elements 110 when the assembly 100 is under compression. The collar 140 includes a split 142 that allows the collar 140 to compress under load, preferably elastically. The collar 140 also includes an inner bore 144 of sufficient size to fit over the rod elements 110, or if the sheath 120 is attached, over the outside of the sheath 120 such that the collar 140 is compressible under load. The thickness of the wall 146 of the collar 140 affects the flexibility and strength of the collar 140.

The inner bore 144 is of sufficient size to allow the collar 140 to slide to the proper position; however, the inner bore 144 may be undersized to apply a force to, or spring against, the rod elements 110 or sheath 120 to allow the collar 140 to maintain its location after positioning on the rod elements 110 or the sheath 120. The collar 140 is provided with the spilt 142 to allow uniform or semi-uniform compression of the rod elements 110.

By providing the collar 140, the rigidity of the entire assembly 100 is increased. This is important for spanning longer distances, such as when the implants are spread over non-consecutive levels. The longer the distance the rod elements 110 are unsupported, the more flexible the assembly 100 becomes between the fixation points. The collar 140 adds rigidity and binds the rod elements 110 and/or the sheath 120 together. The collar 140 is designed to slide over the rod elements 110 from any position along the rod elements 110, such as between spinal components after locking. This also allows a means of increasing stiffness of the assembly 100 at the end of the surgical procedure. In addition, the collar 140 may provide a means for another component to be added to the assembly 100, such as a rod-to-rod connector, or a transverse connector, to connect two rod assemblies together.

It is also possible to use a collar that does not have a split (not shown), but is simply a section of a thin wall tube. By compressing against the rod elements 110, the thin wall is pushed inward against the rod elements 110, effectively creating a crimp that secures the rod elements 110 against each other and holds the rod elements 110 securely within the spinal assembly 100.

Figure 4:
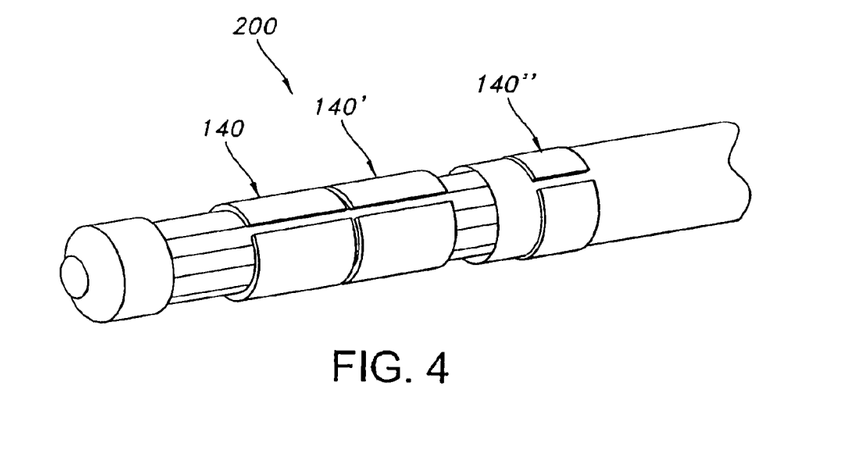
FIG. 4 is a perspective view of a spinal rod assembly according to a second embodiment of the present invention.

The use of the collar 140 is optional, but as many as needed may be used. For example, in an alternate embodiment of a spinal rod assembly 200, shown in FIG. 4, an additional collar 140' and/or collar 140" may be added to the collar 140. Although three collars 140, 140', 140" are shown, those skilled in the art will recognize that more or less than three collars 140, 140', 140" may be used.

Figure 5:
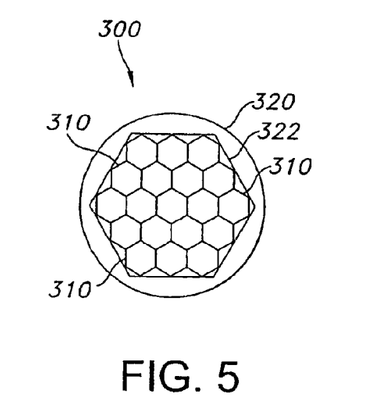
FIG. 5 is an end profile view of a spinal rod assembly according to a third embodiment of the present invention.

In an alternative embodiment of a spinal rod assembly 300, shown in FIG. 5, rod elements 310 may have a generally hexagonal cross section. The hexagonal cross section of the rod elements 310 increases the cross sectional area of the assembly 300 compared to the circular cross section of the rod elements 110, without increasing the size of the assembly 300. Such increase in cross sectional area provides increased strength without increasing the exterior size of the assembly 300. Although rod elements 110 having a circular cross section and rod elements 310 having a hexagonal cross section are shown, those skilled in the art with the aide of this disclosure will recognize that rod elements may have other cross sectional shapes, such as square, oval, or any other suitable shape.

Further, as seen in the assembly 300, a sheath 320 may include a non-circular interior cross section, such as the hexagonal interior cross section 322 shown in FIG. 5.

Figure 6:
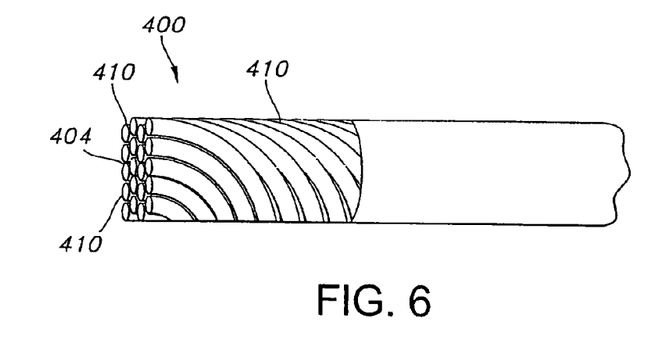
FIG. 6 is a perspective view of a spinal rod assembly according to a fourth embodiment of the present invention.

Although FIG. 1 shows the rod elements 110 extending in a straight, parallel line, FIG. 6 shows a spinal rod assembly 400 that uses rod elements 410 that are helically wrapped around each other. This helical winding forces the rod elements 410 into compression and provides a more rigid structure. One method of winding the rod elements 410 is by winding the external rod elements 410 around the center axis or center rod element 410, such that the rod elements 410 come in contact with each other and become more rigid. This approach may be performed as part of the initial manufacturing procedure, or at the time of surgery, in vivo. During manufacturing, the helical winding may be made in a manner to bind the various rod elements 410 together without the need for an external sheath. During surgery, after insertion of the rod assembly into the spinal implants, such as screws and hooks, the rod elements 410 can be turned into a helical wind by grasping the bundle of rod elements 410 at the proximal end 402 of the assembly 400 and twisting. This action then creates a more rigid structure, as it forces the individual rod elements 410 to contact each other without the use of external collars. Thus, multiple ways exist to adjust the assembly rigidity and design to meet various requirements.

Although FIG. 6 shows a rod assembly 400 without a tip, those skilled in the art with the aide of this disclosure will recognize that a tip (not shown) may be affixed to a distal end 404 of the rod assembly 400 as described above with respect to the tip 130. Further, a collar (not shown) may be disposed around the rod elements 410.

Figure 7:
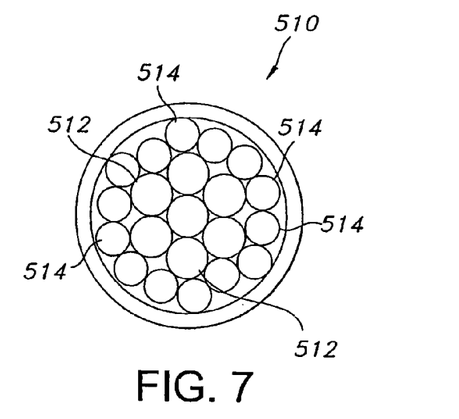
FIG. 7 is an end profile view of a spinal rod assembly according to a fifth embodiment of the present invention.

Also, although FIGS. 1, 5, and 6 show rod elements 110, 310, 410 that are all the same size, those skilled in the art with the aide of this disclosure will recognize that the rod elements, such as rod elements 510, shown in FIG. 7, need not necessarily all be the same size. As shown a spinal rod assembly 500, inner elements 512 are of a substantially larger cross sectional size than outer elements 514. However, it is within the scope of the present invention that the outer elements may be of a substantially larger cross section than the inner elements.

Figure 8:
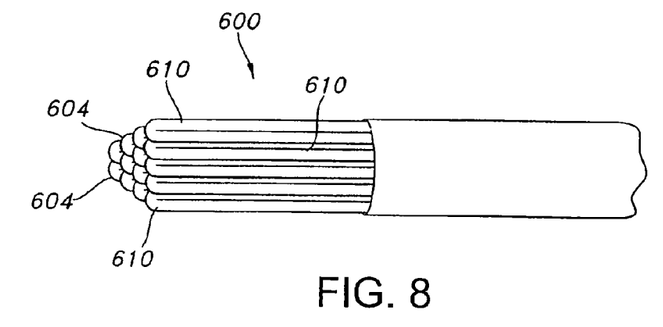
FIG. 8 is a perspective view of a spinal rod assembly according to a sixth embodiment of the present invention.
Figure 9:
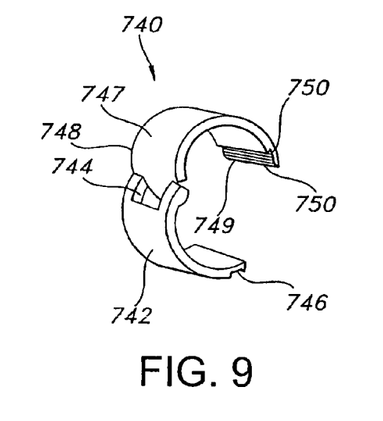
FIG. 9 is a perspective view of a locking collar for use in a spinal rod assembly according to a seventh embodiment of the present invention, with the locking collar in an "open" position.

Alternatively, as shown in FIG. 8, a rod assembly 600 may also be formed by folding over a single longer rod element 610. This provides two rod elements 610 that are naturally fixed at the tip 630, or bend point. It is possible to use one or more of these folded rod elements 610 to form the rod assembly 600. Although FIG. 8 shows a rod assembly 600 without a separate tip member, those skilled in the art with the aide of this disclosure will recognize that a tip (not shown) may be affixed to a distal end 604 of the rod assembly 600 as described above with respect to the tip 130. Further, a collar (not shown) may be disposed around the rod elements 610.

In an alternative embodiment of a spinal rod assembly 700, a ratcheting collar 740, shown in FIGS. 9-12, is used to wrap around rod elements 710. The ratcheting collar 740 includes a generally semi-cylindrically shaped first member 742 that has a first hinge portion 744. The first member 742 also includes a pawl 746 that is located distally from the first hinge portion 744. The ratcheting collar 740 also includes a generally semi-cylindrically shaped second member 747 that has a second hinge portion 748 that hingedly connects to the first hinge portion 744 and allows the first and second members 742, 747 to pivot with respect to each other. The second member 747 also includes a ratchet 749 having a plurality of teeth 750.

Figure 10:
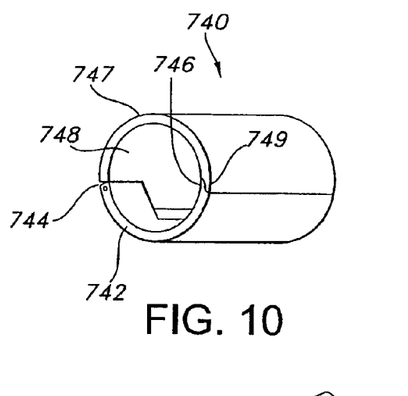
FIG. 10 is a perspective view of the locking collar of FIG. 9, with the locking collar in a "closed" position.
Figure 11:
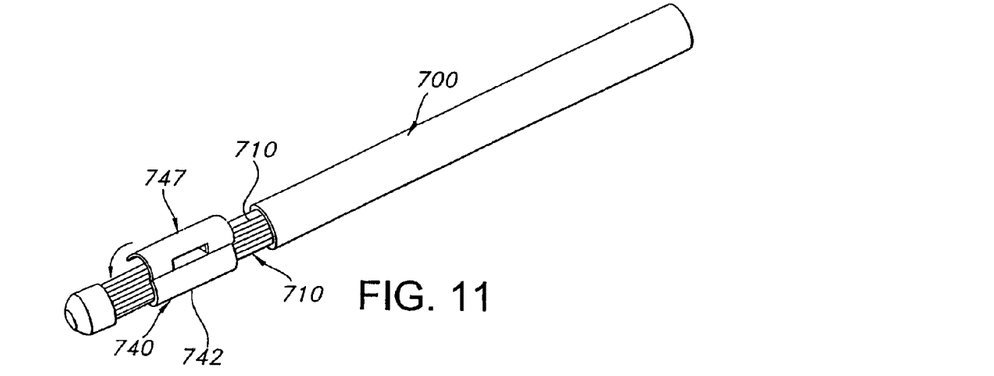
FIG. 11 is a perspective view of the locking collar of FIG. 9 being disposed about a spinal rod assembly.
Figure 12:
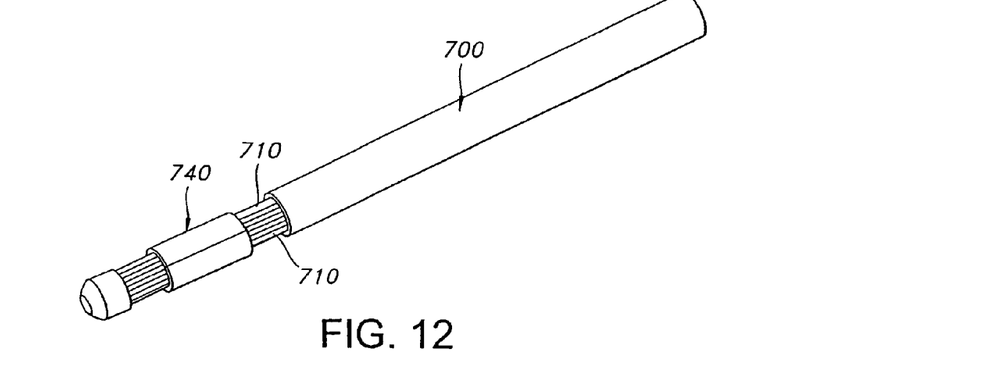
FIG. 12 is a perspective view of the locking collar of FIG. 9 having disposed about a spinal rod assembly.

When the collar 740 is pivoted to a closed position, as shown in FIG. 11, the ratchet teeth 750 engage the pawl 746 (as shown in FIG. 10), until sufficient force is exerted against the rod elements 710, strengthening the assembly 700.

Figure 13:
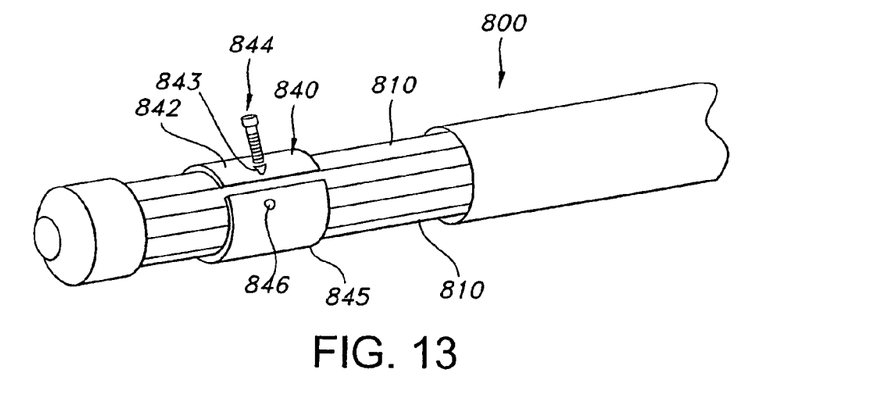
FIG. 13 is a perspective view of a locking collar for use in a spinal rod is assembly according to an eighth embodiment of the present invention.
Figure 14:
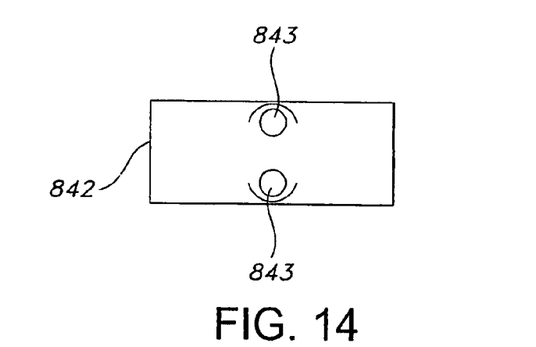
FIG. 14 is a top plan view of a top portion of the locking collar shown in FIG. 13.
Figure 15:
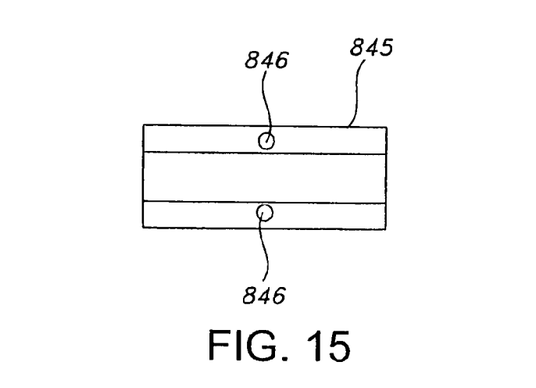
FIG. 15 is a top plan view of a bottom portion of the locking collar shown in FIG. 13.

Yet another embodiment of a collar 840 used in a rod assembly 800 is shown in FIGS. 13-15. The collar 840 includes a generally semi-cylindrically shaped first member 842 that includes passages 843 to allow a screw 844 to pass through. Preferably, at least one passage 843 is aligned on either side of the first member 842 to allow the screw 844 to pass through the passage 843 in either side of the rod elements 810. The collar 840 further includes a generally semi-cylindrically shaped second member 845 that mates with the first member 842. The second member 845 includes threaded recesses 846 that each match up with a respective passage 843 to receive the screw 844 after the screw 844 passes through its respective passage 843.

The first member 842 and the second member 845 are mated together, with the rod elements 810 disposed within the cavity formed by the mating members 842, 845. The screws 844 are inserted through their respective passages 843 and threaded into threaded recesses 846 to retain the first and second members 842, 845 to each other, around the rod elements 810.

Figure 16:
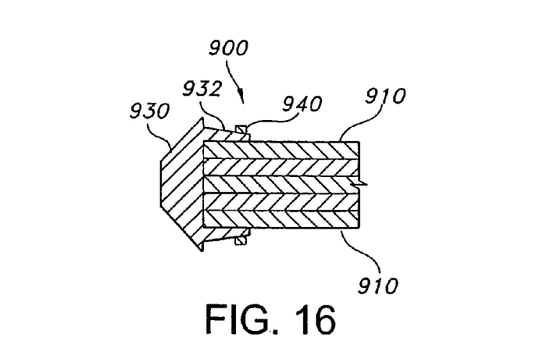
FIG. 16 is a sectional view of a distal tip of a spinal rod assembly according to a ninth embodiment of the present invention.

In another alternative embodiment of a rod assembly 900, shown in FIG. 16, compression can be exerted by providing a tip 930 with a threaded portion 932, such that the threaded portion 932 is over a distal end of rod elements 910. By tightening an external nut 940, the threads of the nut 940 and the threaded portion 932 are engaged, which exerts a compressive force against the rod elements 910. This force can be particularly effective when the threads are tapered, so that the further the nut 940 is tightened, the more compressive force is exerted.

Figure 17:
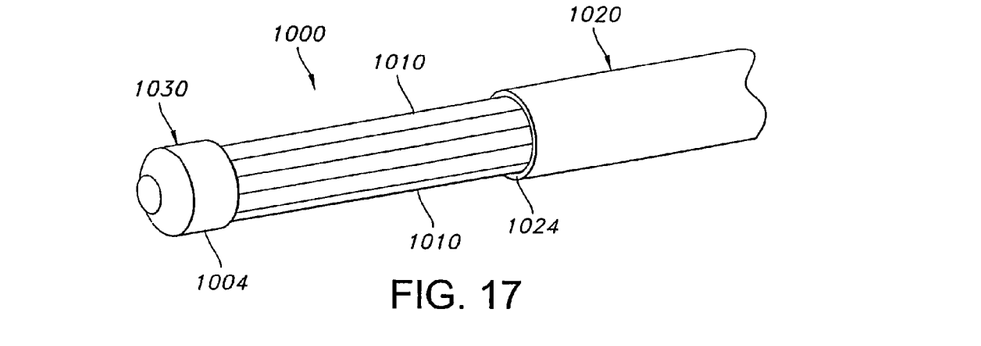
FIG. 17 is a perspective view of a spinal rod assembly according to a tenth embodiment of the present invention, with a sheath in a first position.
Figure 18:
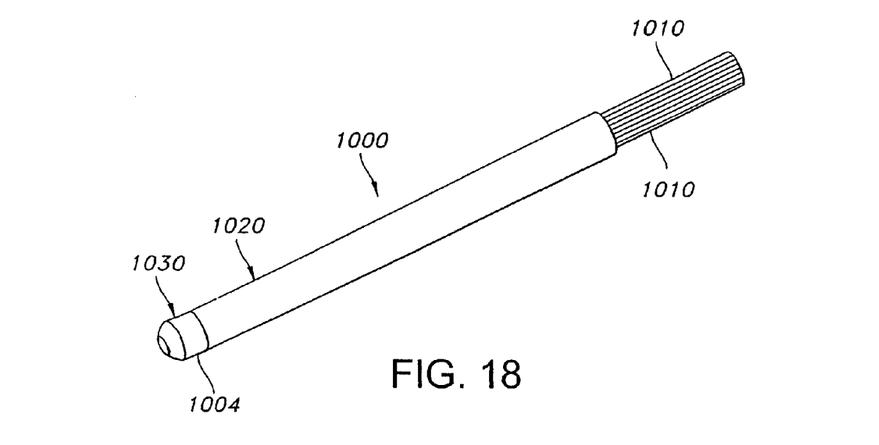
FIG. 18 is a perspective view of the spinal rod assembly shown in FIG. 17, with the sheath in a second position.

In still another embodiment of a rod assembly 1000, shown in FIGS. 17 and 18, the rod assembly 1000 may omit a collar and provide a flexible sheath 1020 that is slidable along a length of rod elements 1010. A distal end 1022 of the sheath 1020 may include a lip 1024 that is insertable into a tip 1030, as shown in FIG. 18. The slidable sheath 1020 provides additional strength to the distal end 1004 of the rod assembly 1000.

Figure 19:
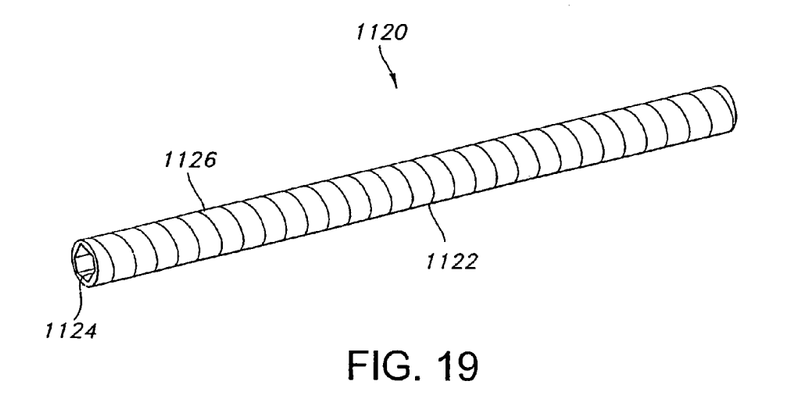
FIG. 19 is a perspective view of an alternative embodiment of a sheath of the present invention.

FIG. 19 shows an alternative embodiment of a sheath 1120 that may be used with any of the embodiments of the rod assemblies 100-1000 described above. Sheath 1120 includes a generally helical elongated strip 1122 that forms a tubular shape. The helical nature of the sheath 1120 provides flexibility for the sheath 1120 to allow the sheath 1120 to bend with the rod elements that are contained within the sheath 1120. In an exemplary embodiment, sheath 1120 is constructed from titanium, although those skilled in the art will recognize that other biocompatible material may be used.

Sheath 1120 includes a generally hexagonal interior cross section 1124, similar to the cross section shown in FIG. 5. The generally hexagonal cross section 1124 reduces wasted space within the sheath 1120 between the rod elements and the sheath 1124, providing additional strength to the sheath 1120.

In an exemplary method of manufacturing the sheath 1120, a solid cylinder of material, such as titanium, is provided. A helical cut 1126 is formed in the exterior of the cylinder, starting approximately 1 millimeter from a distal end of the cylinder and ending approximately 1 millimeter from a proximal end of the cylinder. Both the proximal and distal ends of the cylinder remain uncut to eliminate any sharp edges that may damage tissue. The interior of the cylinder is EDM machined to form the hexagonal cross section 1124. The machining of the interior extends far enough toward the exterior of the cylinder to intersect the helical cut 1126 and to form the strip 1122.

The sheath 1120 can be inserted over the rod elements as described above with respect to sheath 120. The helical nature of the sheath 1120 allows the sheath 1120 to better flex with the flexing of the rod elements during insertion of the rod assembly into the patient. It is anticipated that the sheath 1120 remains in the patient after insertion, with a set screw (not shown) proximate to each of the proximal and distal ends of the sheath 1120 that tightens the sheath 1120 against the rod elements within the sheath 1120 and strengthens the rod assembly.

Although the embodiments of the rod assemblies 200-1000 described above all include at least one feature that deviates in some way from the first embodiment of the rod assembly 100, those skilled in the art with the aide of this disclosure will recognize that yet other embodiments are envisioned that include combinations of these embodiments.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A self-contouring spinal rod assembly comprising:
a plurality of parallel rod elements directly contacting one another in slidable engagement, the spinal rod assembly having a proximal end, a distal end, and a length extending between the proximal and distal ends; and
a sheath extending over the plurality of rod elements between the distal end and the proximal end, the sheath having an outer perimeter that is circular in cross section, the circular outer perimeter extending uniformly along the length of the sheath,
wherein the plurality of rod elements extend along the length such that each of the plurality of rod elements is in contact with an adjacent rod element, the plurality of rod elements are fixed against movement relative to each other at the distal end, and the plurality of rod elements are movable relative to each other along a length proximal the distal end, the distal end comprising a tip, the tip comprising a cylindrical tubular cap having an open end and a closed end, the cap forming a bore exposed at the open end, the ends of the rod elements received through the open end and into the bore, the ends fixed in the bore against movement relative to each other at the distal end.

2. The self-contouring spinal rod assembly of claim 1, wherein at least one rod element of the plurality of rod elements has a generally circular cross section.

3. The self-contouring spinal rod assembly of claim 1, wherein at least one rod element of the plurality of rod elements has a generally hexagonal cross section.

4. The self-contouring spinal rod assembly of claim 1, wherein at least a first rod element of the plurality of rod elements is larger in diameter than at least a second rod element of the plurality of rod elements.

5. The self-contouring spinal rod assembly of claim 1, wherein the tip is fixedly connected to the distal end.

6. The self-contouring spinal rod assembly of claim 1, wherein the sheath is wrapped around the plurality of rod elements between the distal end and the proximal end.

7. The self-contouring spinal rod assembly of claim 6, wherein the sheath is removable from the plurality of rod elements.

8. The self-contouring spinal rod assembly of claim 6, wherein the sheath is fixedly connected to the distal end.

9. The self-contouring spinal rod assembly of claim 6, wherein the sheath comprises a non-circular interior cross section.

10. The self-contouring spinal rod assembly of claim 6, wherein the sheath comprises a helically wound elongated strip.

11. The self-contouring spinal rod assembly of claim 1, further comprising a collar disposed about the plurality of rod elements proximal the distal end.

12. The self-contouring spinal rod assembly of claim 11, wherein the collar comprises a split collar.

13. The self-contouring spinal rod assembly of claim 11, wherein the collar comprises a locking collar.

14. The self-contouring spinal rod assembly of claim 13, wherein the locking collar comprises a ratchet.

15. The self-contouring spinal rod assembly of claim 13, wherein the locking collar comprises a screw.

16. The self-contouring spinal rod assembly of claim 1, wherein each of the plurality of rod elements comprises a lubricious coating.

17. A self-contouring spinal rod assembly comprising:
a rod bundle having a distal end, a proximal end, and a length extending between the distal end and the proximal end, the rod bundle comprising a plurality of generally parallel rods directly contacting one another in slidable engagement;
a tip fixedly connected to the distal end; and
a sheath extending over the plurality of rods between the distal end and the proximal end, the sheath having an outer perimeter that is circular in cross section, the circular outer perimeter extending uniformly along the length of the sheath, proximal the distal end,
wherein the tip comprises a cylindrical tubular cap having an open end and a closed end, the cap forming a bore exposed at the open end, the ends of the rods received through the open end and into the bore, the ends of the rods fixed in the bore against movement relative to each other at the distal end.

18. The self-contouring spinal rod assembly of claim 17, wherein the rod bundle comprises at least two rods.

19. The self-contouring spinal rod assembly of claim 18, wherein a first rod is helically wrapped around at least a second rod.

20. The self-contouring spinal rod assembly of claim 17, wherein the sheath is attached to the tip.

21. The self-contouring spinal rod assembly of claim 17, further comprising a collar disposed about the rod bundle between the tip and the sheath.

22. The self-contouring spinal rod assembly of claim 21, wherein the collar comprises a split collar.

23. The self-contouring spinal rod assembly of claim 21, wherein the collar comprises a locking collar.

24. The self-contouring spinal rod assembly of claim 23, wherein the locking collar comprises a ratchet.

25. The self-contouring spinal rod assembly of claim 23, wherein the locking collar comprises a screw.

26. The self-contouring spinal rod assembly of claim 17, wherein the sheath is fixedly connected to the rod bundle.

27. The self-contouring spinal rod assembly of claim 17, further comprising a collar disposed about the sheath.

28. The self-contouring spinal rod assembly of claim 17, wherein the tip comprises a taper.

29. A method of assembling a spinal rod assembly comprising the steps of:
providing a plurality of rod elements;
bundling the plurality of rod elements into a bundle, the rod elements bundled in a generally parallel arrangement and directly contacting one another in slidable engagement;

fixing a tip over the distal ends of the plurality of rod elements to fixedly connect the distal ends of the plurality of rod elements together, the tip comprising a cylindrical tubular cap having an open end and a closed end, the cap forming a bore exposed at the open end, the ends of the rod elements received through the open end and into the bore, the ends fixed in the bore against movement relative to each other at the distal end; and disposing a covering over the plurality of rod elements, proximal the distal ends, the covering having an outer perimeter that is circular in cross section, the circular outer perimeter extending uniformly along the length of the covering.

30. The method of claim 29, wherein the step of disposing a cover over the plurality of rod elements comprises disposing a sheath over the plurality of rod elements.

31. The method of claim 30, wherein the step of disposing the sheath over the plurality of rod elements comprises fixedly connecting the sheath to the plurality of rod elements.

32. The method of claim 29, wherein the step of disposing a cover over the plurality of rod elements comprises disposing a collar over the plurality of rod elements.

33. The method of claim 32, wherein the step of disposing the collar over the plurality of rod elements comprises disposing a split collar over the plurality of rod elements.

34. The method of claim 32, wherein the step of disposing the collar over the plurality of rod elements comprises disposing a ratcheting collar over the plurality of rod elements.

35. The method of claim 32, wherein the step of disposing the collar over the plurality of rod elements comprises securing the collar to the rod elements with a screw.

36. The method of claim 29, wherein the step of fixing a tip over the distal ends of the plurality of rod elements comprises the step of fixing the cap over the distal ends by thermal expansion and contraction.

37. The method of claim 29, wherein the step of fixing a tip over the distal ends of the plurality of rod elements comprises the step of welding the cap to the rod elements.

38. The method of claim 29, wherein the step of fixing a tip over the distal ends of the plurality of rod elements comprises the step of mechanically compressing the cap around the distal ends.

\* \* \* \* \*